(12) United States Patent
Guan et al.

(10) Patent No.: US 10,558,845 B2
(45) Date of Patent: Feb. 11, 2020

(54) APPARATUS AND METHOD FOR DETERMINATION OF MEDICATION LOCATION

(75) Inventors: Lei Guan, Philadelphia, PA (US); Adam Hanina, New York, NY (US)

(73) Assignee: AIC Innovations Group, Inc., New York, NY (US)

( * ) Notice: Subject to any disclaimer, the term of this patent is extended or adjusted under 35 U.S.C. 154(b) by 487 days.

(21) Appl. No.: 13/214,201

(22) Filed: Aug. 21, 2011

(65) Prior Publication Data

US 2013/0044196 A1    Feb. 21, 2013

(51) Int. Cl.
| | | |
|---|---|---|
| G06Q 10/00 | (2012.01) |
| G06K 9/00 | (2006.01) |
| A61B 5/00 | (2006.01) |
| A61B 5/11 | (2006.01) |

(52) U.S. Cl.
CPC ........ *G06K 9/00221* (2013.01); *A61B 5/0022* (2013.01); *A61B 5/1128* (2013.01); *A61B 5/4833* (2013.01)

(58) Field of Classification Search
CPC ... G06K 9/00221; G06F 19/324; G06Q 50/22
USPC .......................................................... 348/77
See application file for complete search history.

(56) References Cited

U.S. PATENT DOCUMENTS

| | | | |
|---|---|---|---|
| 3,814,845 A | 6/1974 | Hurlbrink et al. |
| 5,065,447 A | 11/1991 | Barnsley et al. |
| 5,441,047 A | 8/1995 | David et al. |
| 5,486,001 A * | 1/1996 | Baker ................ A63B 24/0003 |
| | | | 434/252 |
| 5,544,649 A | 8/1996 | David et al. |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brudny et al. |
| 5,911,132 A | 6/1999 | Sloane |
| 5,961,446 A | 10/1999 | Beller et al. |
| 6,151,521 A | 11/2000 | Guo et al. |
| 6,233,428 B1 | 5/2001 | Fryer |

(Continued)

FOREIGN PATENT DOCUMENTS

EP        2048615 A1    4/2009

OTHER PUBLICATIONS

Face and hands detection and tracking applied to the monitoring of medication intake; 2008.*

(Continued)

*Primary Examiner* — Luis Perez-Fuentes
(74) *Attorney, Agent, or Firm* — Fish & Richardson P.C.

(57) ABSTRACT

A method, apparatus and computer program stored on a non-volatile computer readable storage medium for confirming a pill in the mouth of a user. The computer program causing a general purpose computer to perform the steps of capturing one or more images of a user by an image capture device, confirming the position of the face of the user within the captured image by measuring a size of the face, and setting a predetermined portion of the face of the user to be a region of interest. An open mouth of the user is confirmed within the region of interest, and the open mouth of the user is classified as one of a mouth with a pill therein and a mouth without a pill therein.

18 Claims, 5 Drawing Sheets

(56) References Cited

U.S. PATENT DOCUMENTS

| | | |
|---|---|---|
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1 | 3/2003 | Wootton et al. |
| 6,611,206 B2 | 8/2003 | Eshelman et al. |
| 6,696,924 B1* | 2/2004 | Socinski ............ G06F 19/3456 700/213 |
| 6,705,991 B2 | 3/2004 | Bardy |
| 6,879,970 B2 | 11/2005 | Shiffman et al. |
| 6,988,075 B1 | 1/2006 | Hacker |
| 7,062,312 B2* | 6/2006 | Gonzales ............ A61K 49/0004 424/9.7 |
| 7,184,047 B1 | 2/2007 | Crampton |
| 7,184,075 B2 | 2/2007 | Reiffel |
| 7,228,203 B2* | 6/2007 | Koselka ............... B25J 5/007 318/568.12 |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,395,214 B2* | 7/2008 | Shillingburg ....... G06F 19/3462 705/2 |
| 7,415,447 B2 | 11/2008 | Shiffman et al. |
| 7,448,544 B1 | 11/2008 | Louie et al. |
| 7,469,213 B1* | 12/2008 | Rao ................. G06F 19/3462 705/2 |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,693,729 B2* | 4/2010 | Yankelevitz ............ G06Q 50/22 705/2 |
| 7,747,454 B2* | 6/2010 | Bartfeld et al. ............... 705/3 |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2 | 1/2011 | Elsayed et al. |
| 7,881,537 B2 | 2/2011 | Ma et al. |
| 7,908,155 B2 | 3/2011 | Fuerst et al. |
| 7,912,733 B2 | 3/2011 | Clements et al. |
| 7,956,727 B2 | 6/2011 | Loncar |
| 7,983,933 B2 | 7/2011 | Karkanias et al. |
| 8,155,887 B2* | 4/2012 | Rothschild ............ G06F 19/326 702/19 |
| 8,218,143 B2* | 7/2012 | Gupta ................ A61B 5/0097 356/326 |
| 8,321,284 B2 | 11/2012 | Clements et al. |
| 8,448,846 B2* | 5/2013 | Needham ............ G06F 19/3456 235/375 |
| 8,560,098 B1* | 10/2013 | Chapman ............... G01F 1/00 700/83 |
| 9,183,601 B2* | 11/2015 | Hanina .................. G06Q 50/22 |
| 9,399,111 B1* | 7/2016 | Hanina ................. A61M 21/02 |
| 9,665,767 B2* | 5/2017 | Guan ................. G06K 9/00355 |
| 2001/0049673 A1 | 12/2001 | Dulong et al. |
| 2001/0056358 A1 | 12/2001 | Dulong et al. |
| 2002/0026330 A1 | 2/2002 | Klein |
| 2002/0093429 A1 | 7/2002 | Matsushita et al. |
| 2002/0143563 A1 | 10/2002 | Hufford et al. |
| 2003/0158756 A1* | 8/2003 | Abramson ............ G06F 19/324 705/3 |
| 2003/0164172 A1 | 9/2003 | Chumas et al. |
| 2003/0190076 A1 | 10/2003 | Delean |
| 2003/0194374 A1* | 10/2003 | Heasley et al. ............... 424/9.1 |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2005/0038326 A1* | 2/2005 | Mathur ..................... 600/300 |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0233459 A1* | 10/2005 | Melker et al. .................. 436/56 |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2007/0008112 A1 | 1/2007 | Covannon et al. |
| 2007/0008113 A1 | 1/2007 | Spoonhower et al. |
| 2007/0030363 A1 | 2/2007 | Cheatle et al. |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0273504 A1* | 11/2007 | Tran ..................... 340/539.12 |
| 2008/0000979 A1 | 1/2008 | Poisner |
| 2008/0162192 A1 | 3/2008 | Vonk et al. |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0138604 A1 | 6/2008 | Kenney et al. |
| 2008/0140444 A1 | 6/2008 | Karkanias et al. |
| 2008/0178126 A1 | 7/2008 | Beeck et al. |
| 2008/0201174 A1 | 8/2008 | Ramasubramanian et al. |
| 2008/0219493 A1 | 9/2008 | Tadmor |
| 2008/0275738 A1* | 11/2008 | Shillingburg ....... G06F 19/3462 705/3 |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0043610 A1 | 2/2009 | Nadas et al. |
| 2009/0048871 A1 | 2/2009 | Skomra |
| 2009/0095837 A1 | 4/2009 | Lindgren |
| 2009/0128330 A1 | 5/2009 | Monroe |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1* | 2/2010 | Bartfeld ............... G06F 19/3456 705/2 |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0135907 A1* | 6/2010 | Cranley et al. ............... 424/9.1 |
| 2010/0136509 A1 | 6/2010 | Mejer et al. |
| 2010/0138154 A1 | 6/2010 | Kon |
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0119073 A1 | 5/2011 | Hanina .................. G06Q 50/22 705/2 |
| 2011/0153360 A1* | 6/2011 | Hanina .................. G06Q 10/10 705/3 |
| 2011/0161109 A1 | 6/2011 | Pinsonneault et al. |
| 2011/0195520 A1 | 8/2011 | Leider et al. |
| 2011/0275051 A1 | 11/2011 | Hanina et al. |
| 2012/0009555 A1* | 1/2012 | Hanina ............... G06F 19/3456 434/262 |
| 2012/0075464 A1 | 3/2012 | Derenne et al. |
| 2012/0086827 A1* | 4/2012 | Hanina .................. A61B 5/004 348/222.1 |
| 2012/0219176 A1* | 8/2012 | Guan ................. G06K 9/00355 382/103 |
| 2013/0044196 A1* | 2/2013 | Guan ................. G06K 9/00221 348/77 |

(56) References Cited

U.S. PATENT DOCUMENTS

| | | | | |
|---|---|---|---|---|
| 2013/0169781 | A1* | 7/2013 | Hanina | G06K 9/00335 348/77 |
| 2014/0063242 | A1* | 3/2014 | Hanina | A61B 5/004 348/143 |
| 2014/0184772 | A1* | 7/2014 | Hanina | G06F 19/3418 348/77 |

OTHER PUBLICATIONS

Real time detection, tracking and recognition of medication intake; Huynh; 2009.*
A computer vision System for monitoring medication intake; Batz.*
Face, hands detection, tracking applied to monitoring of medication intake; Ammouri; 2008. (Year: 2008).*
Face, hands detection, tracking applied monitor of medication intake; Ammouri; 2008. (Year: 2008).*
Real time detection, tracking and recognition of medication intake; Huynh; 2009. (Year: 2009).*
NPL Internet Search log; 2019. (Year: 2019).*
Danya, "Pilot Study Using Video Call Phones for Mobile Direct Observation Treatment (MDOT) to Monitor Medication Compliance of TB Patients", www.danya.com/MDOT.asp, (Mar. 20, 2009).
Guideline, "2008 Patient Adherence Update: New Approaches for Success", www.guideline.com, The Trend Report Series,(Oct. 1, 2008).
GuideView, "GuideView", www.sahs.uth.tme.edu/MSriram/GuideView/, (Mar. 15, 2007).
Osterberg, Lars et al., "Adherence to Medication", *N. Engl J Med* 2005;353:487-97, (Aug. 4, 2005).
Chen, Pauline W., "Texting as a Health Tool for Teenagers", *The New York Times* http://www.nytimes.com/2009/11/05/health//05chen.html?_r=1&emc=, (Nov. 5, 2009).
"Global Tuberculosis Control: A short update to the 2009 report", *World Health Organization*, (2009).
"Super-Resolution", *Wikipedia*, (Oct. 5, 2010).
"PCT Search report and written opinion", (dated Jan. 12, 2011),1-9.
"Non-Final Office Action from PTO", (dated Oct. 13, 2011),1-74.
Non-Final Office Action from PTO, (U.S. Appl. No. 13/558,377), (dated Oct. 22, 2012), 1-21.
Final Office Action from PTO, (U.S. Appl. No. 13/558,377), dated May 7, 2013, 1-29.
Non-Final Office Action from PTO, (U.S. Appl. No. 13/558,380), (dated Oct. 4, 2012), 1-20.
Wang et al. "Recent Developments in human motion analysis." Pattern Recognition 36 (220) 585-601 (Nov. 2001).
Final Office Action from PTO, (U.S. Appl. No. 13/588,380), (dated Mar. 1, 2013), 1-27.
Non-Final Office Action from PTO, (U.S. Appl. No. 12/646,603), (dated Jun. 13, 2013), 1-16.
Non-Final Office Action from PTO, (U.S. Appl. No. 12/728,721), (dated May 9, 2013), 1-25.
Final Office Action from PTO, (U.S. Appl. No. 12/815,037), (dated Sep. 13, 2012), 1-15.
Non-Final Office Action from PTO, (U.S. Appl. No. 12/815,037), (dated Jul. 18, 2013), 1-19.
Non-Final Office Action from PTO, (U.S. Appl. No. 12/899,510), (dated Jan. 23, 2013), 1-20.
Final Office Action from PTO, (U.S. Appl. No. 12/899,510), (dated Aug. 28, 2013).
PCT Search report and written opinion, (PCT/US11/54666), (dated Feb. 28, 2012), 1-13.
Final Office Action from PTO, (U.S. Appl. No. 12/898,338), dated Nov. 9, 2012), 1-12.
PCT Search report and written opinion, (PCT/US11/54668), dated Feb. 28, 2012, 1-12.
Non-Final Office Action from PTO, (U.S. Appl. No. 13/189,518), (dated Dec. 21, 2012), 1-10.
Final Office Action from PTO, (U.S. Appl. No. 13/189,518), (dated Jul. 23, 2013), 1-16.
Non-Final Office Action from PTO, (U.S. Appl. No. 13/235,387), dated Sep. 12, 2013), 1-16.
PCT Search report and written opinion, (PCT/US12/42843), (dated Aug. 31, 2012), 1-8.
PCT Search report and written opinion, (PCT/US2012/051554), (dated Oct. 19, 2012), 1-12.
Huynh et al., "Real time detection, tracking and recognition of medication intake." World Academy of Science, Engineering and Technology 60 (2009), 280-287.
PCT Search report and written opinion, (PCT/US12/59139), (dated Dec. 18, 2012), 1-15.
PCT Search report and written Opinion, (PCT/US13/20026), (dated Aug. 5, 2013), 1-14.
Ammouri, S.; Biloduau, G. -A, "Face and Hands Detectionand Tracking Applied to the Monitoring of Medication Intake," Computer and Robot Vision, 2008. CRV '08. Canadian Conference on, vol. No., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Valin, et al. "Video Surveillance of Medication intake", Int. Conf. of the IEEE Engineering in Medicine and Biology Society, New York City, USA, Aug. 2006.
Bilodeau et al. Monitoring of Medication Intake Using a Camera System. Journal of Medical Systems 2011. [retrieved on Feb. 18, 2013] Retrieved from ProQuest Technology Collection.
Mintchell, "Exploring the Limits of Machine Vision", Automating World, Oct. 1, 2011.
Non-Final Office Action from PTO, (U.S. Appl. No. 12/620,686), (dated Dec. 21, 2011),1-78.
Final Office Action from PTO, (U.S. Appl. No. 12/620,686), (dated May 8, 2012), 1-24.
International Preliminary Report on Patentability, (PCT/US2010/056935), (dated May 31, 2012), 1-8.
Non-Final Office Action from PTO, (U.S. Appl. No. 12/646 383), (dated Dec. 22, 2011),1-78.
Final Office Action from PTO, (U.S. Appl. No. 12/646 383), (dated May 8, 2012), 1-31.
Final Office Action from PTO, (U.S. Appl. No. 12/646,603), (dated Feb. 1, 2012), 1-17.
Non Final Office Action from PTO, (U.S. Appl. No. 12/728,721), (dated Jan. 6, 2012), 1-31.
Final Office Action from PTO, (U.S. Appl. No. 12/728,721), (dated Apr. 12, 2012), 1-31.
Non-Final Office Action from PTO, (U.S. Appl. No. 12/815,037), (dated Mar. 28, 2012),1-17.
PCT Search report and written opinion, (PCT/US2011/35093, (dated Sep. 12, 2011),1-8.
Non-Final Office Action from PTO, (U.S. Appl. No. 12/898,338), (dated Jun. 19, 2012), 1-16.
PCT Search report and written opinion, (PCT/US12/41785, (dated Aug. 17, 2012),1-10.
Aggarwal et al., *Human Activity Analysis: A Review*, ACM Computing Surveys (CSUR), (Apr. 2011) vol. 43, Issue 3, Article No. 16 (47 pages).
Gomez-Conde, et al., *Simple Human Gesture Detection and Recognition Using a Feature Vector and a Real-Time Histogram Based Algorithm*, Journal of Signal and Information Processing, 2:279-286 (2011).
Ijsselmuiden, et al., *Towards High-Level Human Activity Recognition through Computer Vision and Temporal Logic*, KI' 10 Proceedings of the 33rd annual German conference on Advances in artificial intelligence, pp. 426-435 (2010).
Niebles, et al., *Unsupervised Learning of Human Action Categories Using Spatial-temporal Words*, Int J Comput Vis, (Mar. 16, 2007) (20 pages).
Turaga, et al., *Machine Recognition of Human Activities: A survey*, IEEE, 1-15 (2008).

(56) References Cited

OTHER PUBLICATIONS

Extended European Search Report for EP Application No. 12826197.1-1901/2745256—PCT/US2012051554, dated Jan. 15, 2016 (9 pages).

* cited by examiner

APPARATUS AND METHOD FOR DETERMINATION OF MEDICATION LOCATION

FIELD OF THE INVENTION

This invention relates generally to patient compliance in medication administration protocol scenarios, and more particularly to an apparatus and method for confirming whether a patient user has placed a pill in their mouth.

BACKGROUND OF THE INVENTION

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series,* 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication. As has been shown in regards to various public health medication administration situation, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

Traditionally, participants attend introductions and follow ups for clinical trials in-person. Other patients attempting to adhere to a particular medication protocol similarly are given a prescription and a particular set of instructions from a prescribing medical provider or prescribing doctor, and then compliance is measured at a next visit with that prescribing professional through traditional methods of pill counting, and patient interviews. Thus, data collection is similarly limited to patient visits, rather than on a daily basis. These old methods such as patient questioning and pill counting have been proven to be inadequate measures of adherence and offer no information on dose timing and drug holidays (omission of medication for three or more sequential days).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp 1, 763-767, October 2003. To date, technologies alone have only been used to monitor compliance rather than to encourage it. Furthermore, there has been no comprehensive system provided that allows for the management of multiple patients and multiple patient populations. While current technology may allow poor compliers to be recognized, as will be described below, the proposed apparatus and method of the present invention will help to encourage pharmaceutical compliance and tackle some of the problems that are encountered in the clinical trial process in particular, and the medication protocol monitoring problem in general.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact ingesting or otherwise properly administering required medication as required in a clinical drug trial, as prescribed by a prescribing physician in the case where adherence to a particular regimen may prove to be critical to efficacy of the prescription regimen, in various public health scenarios, in situations where failure to keep up a prescription regimen can potentially harm a population as a whole, such as the generation of antibiotic-resistant bacteria strains, in various disease management scenarios, or in home care situations where maintaining proper control of administering healthcare professionals is critical. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Furthermore, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Finally, this system is expensive and requires constant maintenance to confirm that the various mechanical parts are in working order.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant.

Additionally, existing systems fail to maintain an audit trail for post administration review by a medical official or other clinical trial administrator, and further cannot therefore confirm confirmation of proper medication administration or population management.

Therefore, it would be desirable to provide an apparatus that overcomes the drawbacks of the prior art.

SUMMARY OF THE INVENTION

In U.S. patent application Ser. No. 12/620,686, filed Nov. 18, 2009, titled Method and Apparatus for Verification of Medication Administration Adherence; currently pending, U.S. patent application Ser. No. 12/646,383, filed Dec. 23, 2009, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; U.S. patent application Ser. No. 12/728, 721, filed Mar. 22, 2010, titled Apparatus and Method for Collection of Protocol Adherence Data, currently pending, and U.S. patent application Ser. No. 12/815,037, filed Jun. 14, 2010, titled Apparatus and Method for Recognition of Patient Activities When Obtaining Protocol Adherence Data, the contents of these applications being incorporated herein by reference, a proposed system, method and apparatus allows for complete control and verification of adherence to a prescribed medication protocol or machine or apparatus use, whether in a health care provider's care, or when self administered in a homecare situation by a patient.

These applications present the only medication management system that may determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like.

In accordance with an embodiment of the present invention, one or more sequences are provided to be employed in accordance with these or other systems to perform the determination of whether a patient user has placed a pill in their mouth. A first sequence is useful for devices with a lower computing ability, while a second sequence is more applicable to devices with a higher level of computing power.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

The invention will now be described making reference to the following drawings in which like reference numbers denote like structure or steps. While applicable to various platforms, embodiments of the present invention are particularly applicable in situations where resolution of a camera, such as with a web cam, is limited. Also, hardware platforms having limited processing power, such as mobile devices, may benefit from one or more embodiments of the invention.

Figure 1A:
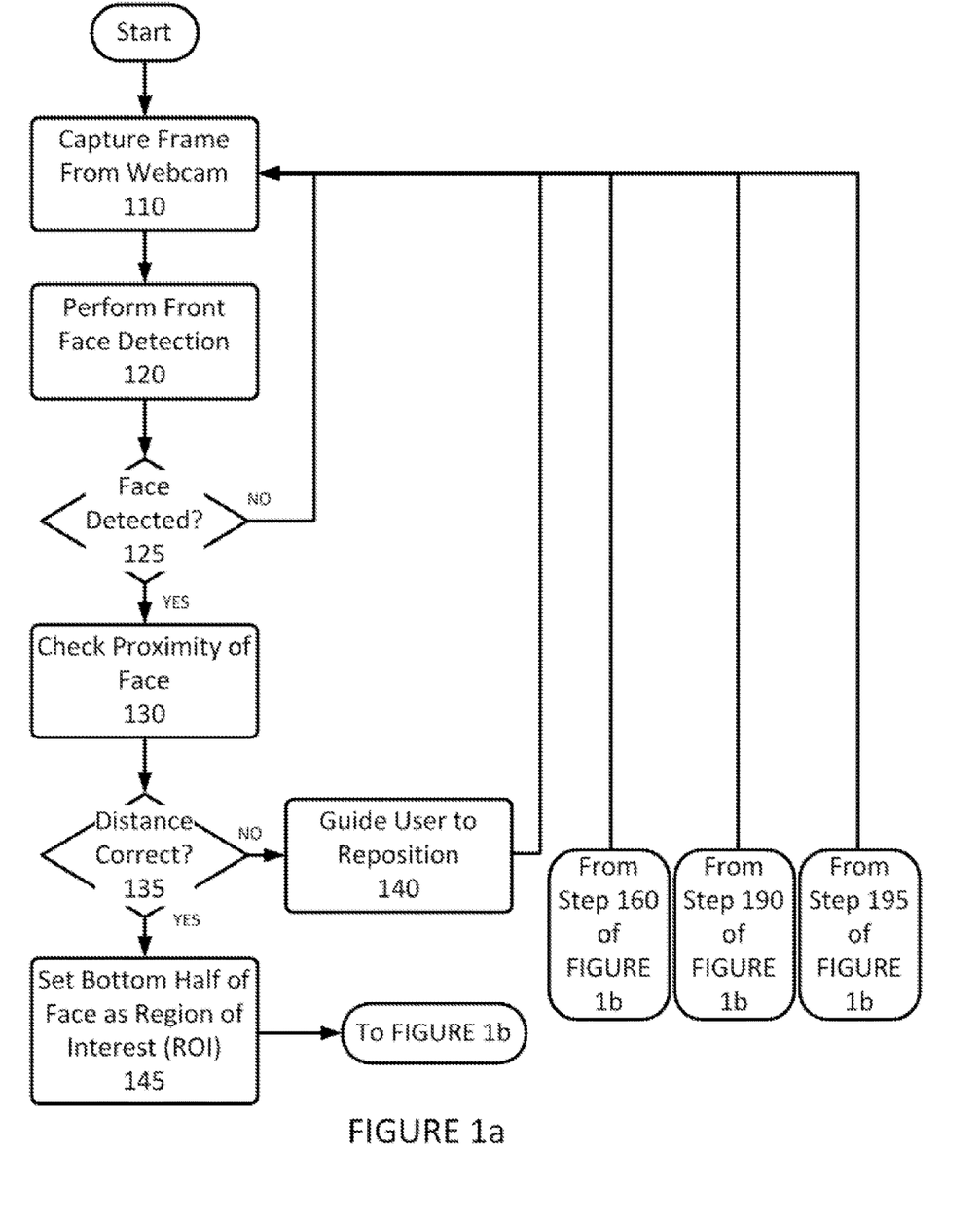
FIGS. 1a and 1b comprise a flow chart diagram depicting a method in accordance with a first embodiment of the invention.
Figure 1B:
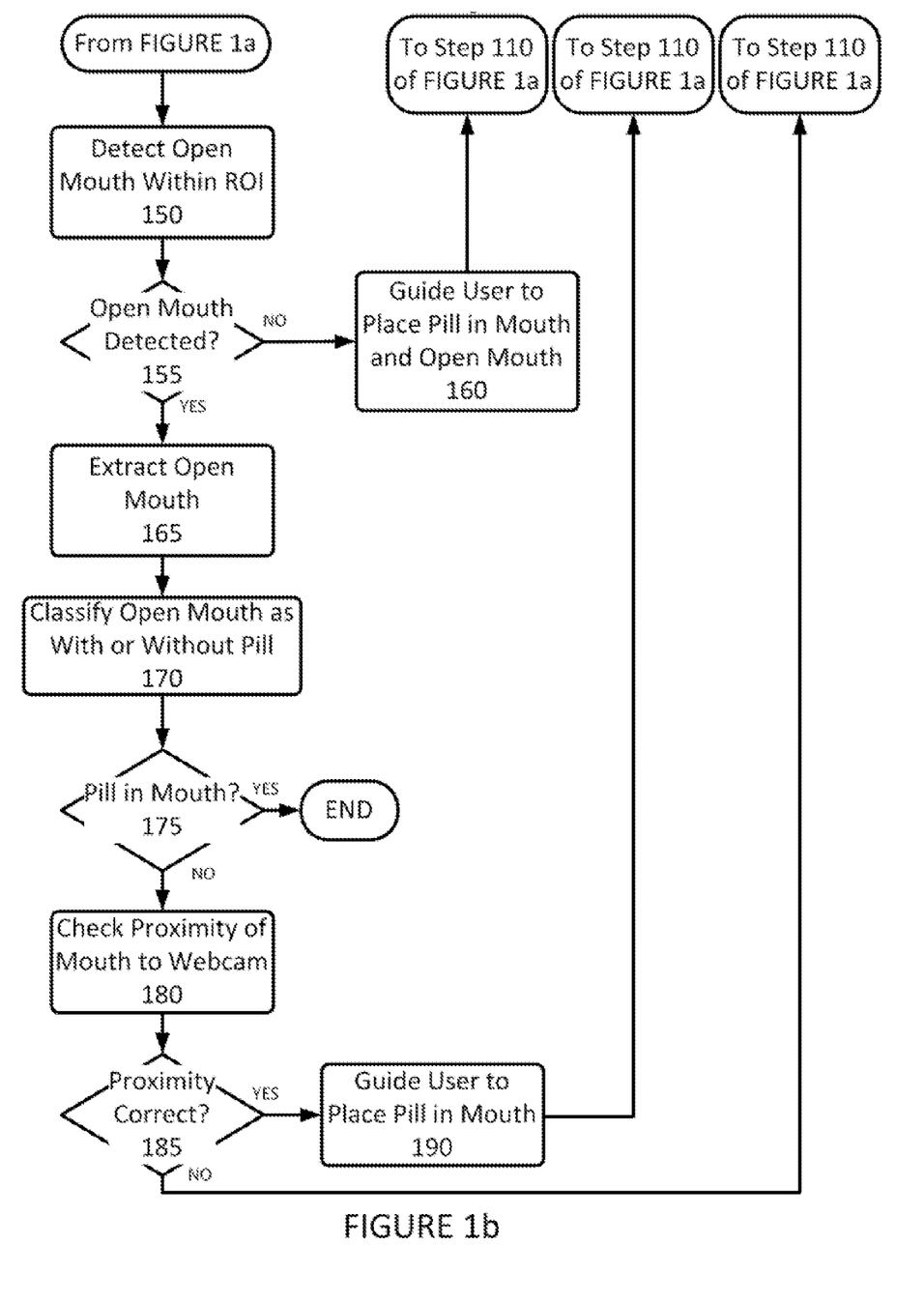

Referring to FIGS. 1a and 1b, a method for determining whether a user has placed a pill in their mouth for use in a less computationally sophisticated environment is presented. While a pill is described herein, any edible object or other item desired to be determined whether in the mouth of a user may be employed in accordance with the invention. Further, various embodiments may also be extended to ingestion or use of other consumables, such as consuming from a bottle or the like. A user is prompted to place a medication pill in their mouth, and at step 110, a frame from a webcam is captured. While this particular embodiment of the invention notes that a single frame is captured, multiple frames may also be captured for use. Next, at step 120, face detection is performed to determine whether a face is present in the field of view. Such face detection is known to those of ordinary skill in the art. At step 125, an inquiry is made as to whether a face is in fact present in the field of view. If this inquiry is answered in the negative, and therefore it is determined that no face is present in the field of view, processing returns to step 110, and one or more additional webcam frames are captured.

If, on the other hand, the inquiry at step 125 is answered in the affirmative, and it is therefore determined that a face is present in the field of view, processing passes to step 130 where the proximity of the face to the webcam is determined by measuring a size of the face in the field of view. After measuring the size of the face, an inquiry is made at step 135 as to whether the face is within a range of correct distances from the webcam. If this inquiry is answered in the negative, and therefore it is determined that the face is not the correct distance from the webcam, processing moves to step 140 where the user is guided to reposition their face, and then processing returns to step 110, and one or more additional webcam frames are captured.

If, on the other hand, the inquiry at step 135 is answered in the positive, and it is therefore determined that the face is the correct distance from the webcam, processing passes to step 145 where the bottom half of the face is set as the Region of Interest (ROI). Processing then passes to step 150, wherein the ROI is searched to determine whether the open mouth of the participant is present. At step 155 an inquiry is made to determine whether an open mouth of the participant has been detected. If this inquiry is answered in the negative, and therefore an open mouth of the participant has not been detected, processing passes to step 160 where the user is guided to place the pill in their mouth (if not already there) and open their mouth. Processing then returns to step 110.

If, on the other hand, the inquiry at step 155 is answered in the affirmative, and it is therefore determined that an open mouth of the user has been detected, processing passes to step 165 where the image of the open mouth of the user is extracted from the image. Once such extraction has taken place, processing passes to step 170 where the open mouth is classified as either an open mouth having a pill therein, or an open mouth not having a pill therein. At step 175 an inquiry is made to determine whether the pill is in the mouth of the user. If this inquiry is answered in the affirmative, and therefore the open mouth was classified at step 170 as an open mouth with a pill therein, then processing is complete, as it has been confirmed that a pill is in the mouth of the user. One or more frames that are captured may additionally be employed in order to determine a confidence with which the determination is made. Thus, various lighting conditions, user movement, or any other factor that may affect the ability of making the classification determination may be employed in order to provide a level of confidence in the classification (i.e. whether the mouth is surely one with a pill, or whether the mouth is probably one with a pill, but the level of confidence in that classification is lower. Based upon such a confidence level, it may be desirable to ask the user to reposition their face relative to the display or camera, to tilt the display or camera or the like. Decision fusion techniques may be employed in order to perform these analyses to include information about the environment, user, pill, etc. to aid in determining confidence levels. Such repositioning may be employed at any time a confidence level determination is made, such determination being employable at any time an analysis of classification of an object is made. In addition to making the general classification decision, it may be desirable in accordance with an embodiment of the invention to allow for further sub-classification in order to rule out possible additional factors. Thus, in the case where the open mouth is classified as an open mouth with a pill therein, it may be desirable to further classify the mouth as showing teeth in addition to the pill, not showing teeth, etc. in order to further aid in the determination of classification of the mouth, and to improve the confidence of any such determination.

One or more additional steps may be employed to further confirm ingestion of the pill by the user. Therefore, it may be confirmed whether the user drinks a glass of water, for example, and/or have the user open their mouth to determine that the pill is no longer in the user's mouth. Classification of the mouth of the user as a mouth without a pill in it may be employed similar to that in step 170 noted above. Once it is determined that the mouth is a mouth without a pill therein, processing can end.

If, on the other hand, the inquiry at step 175 is answered in the negative, and therefore the open mouth was classified in step 170 as an open mouth without a pill therein, processing passes to step 180 where proximity of the mouth of the user to the webcam is determined by measuring a size of the mouth. An inquiry is made at step 185 to determine whether the proximity of the mouth to the web cam is correct in accordance with the measurement of the mouth at step 180. If the inquiry at step 185 is answered in the affirmative, and it is therefore determined that the mouth of the user is a correct distance from the web cam, processing passes to step 190 where the user is guided to place the pill in their mouth (if not already there. Processing then returns to step 110.

If, on the other hand, the inquiry at step 185 is answered in the negative, and it is therefore determined that the mouth of the user is not a correct distance from the web cam, processing then returns to step 110.

Therefore, in accordance with the above-described embodiment of the invention, once the user is properly positioned, determinations are made to determine whether the mouth of the user is open, and to classify such an open mouth in either a first category as being an open mouth with a pill therein, or a second category as being an open mouth without a pill therein. By using such a categorization system, it is not necessary to specifically track the pill, but rather a determination can be made, looking at the mouth as a whole, into which category the mouth should be classified. This simplified process has a number of benefits, including avoiding false positive indications, such as if the mouth is occluded by a hand or the like, being computationally less expensive. By classifying rather than tracking and detecting, less processing power is necessary.

Figure 2A:
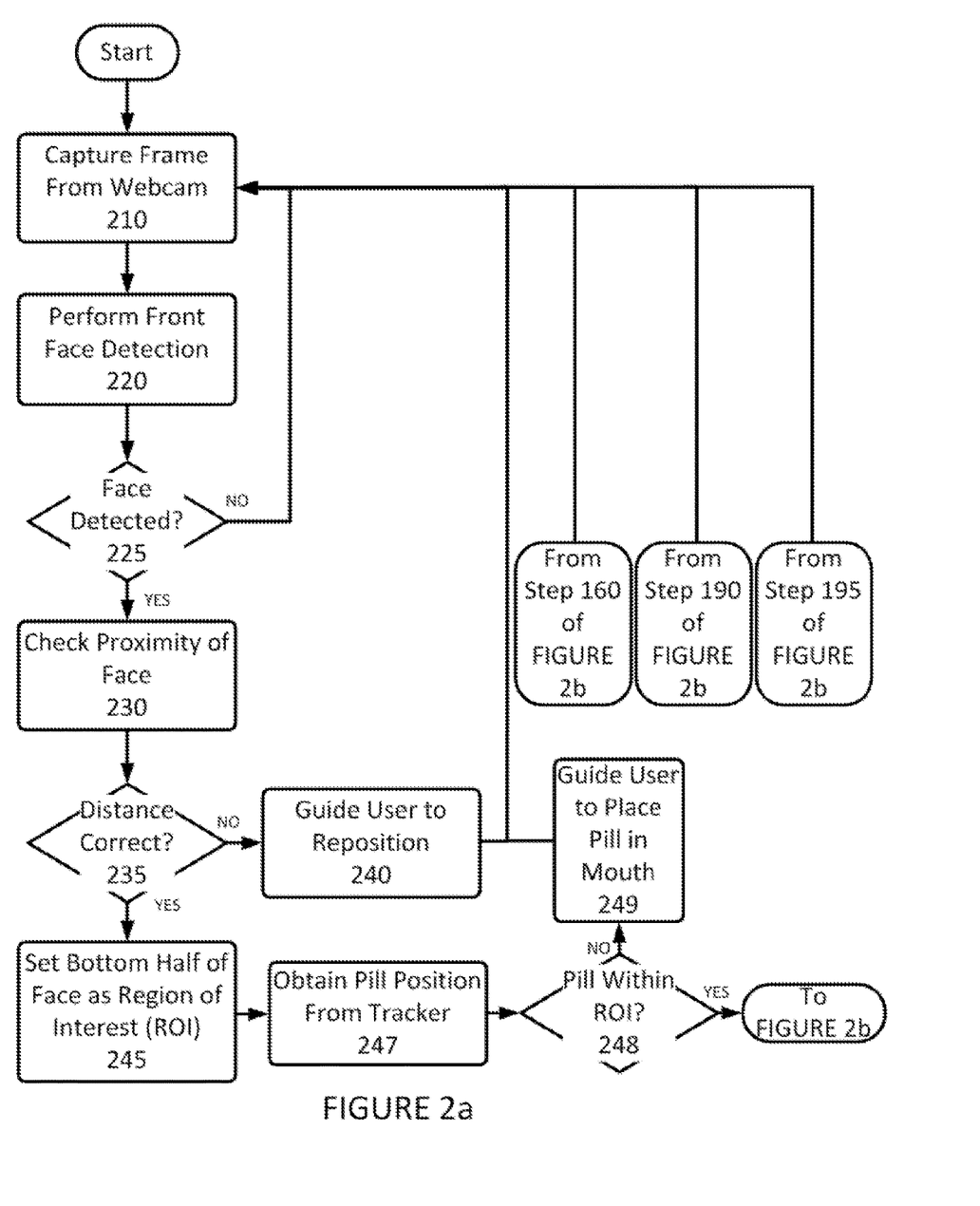
FIGS. 2a and 2b comprise a flowchart diagram depicting a method in accordance with a second embodiment of the invention.
Figure 2B:
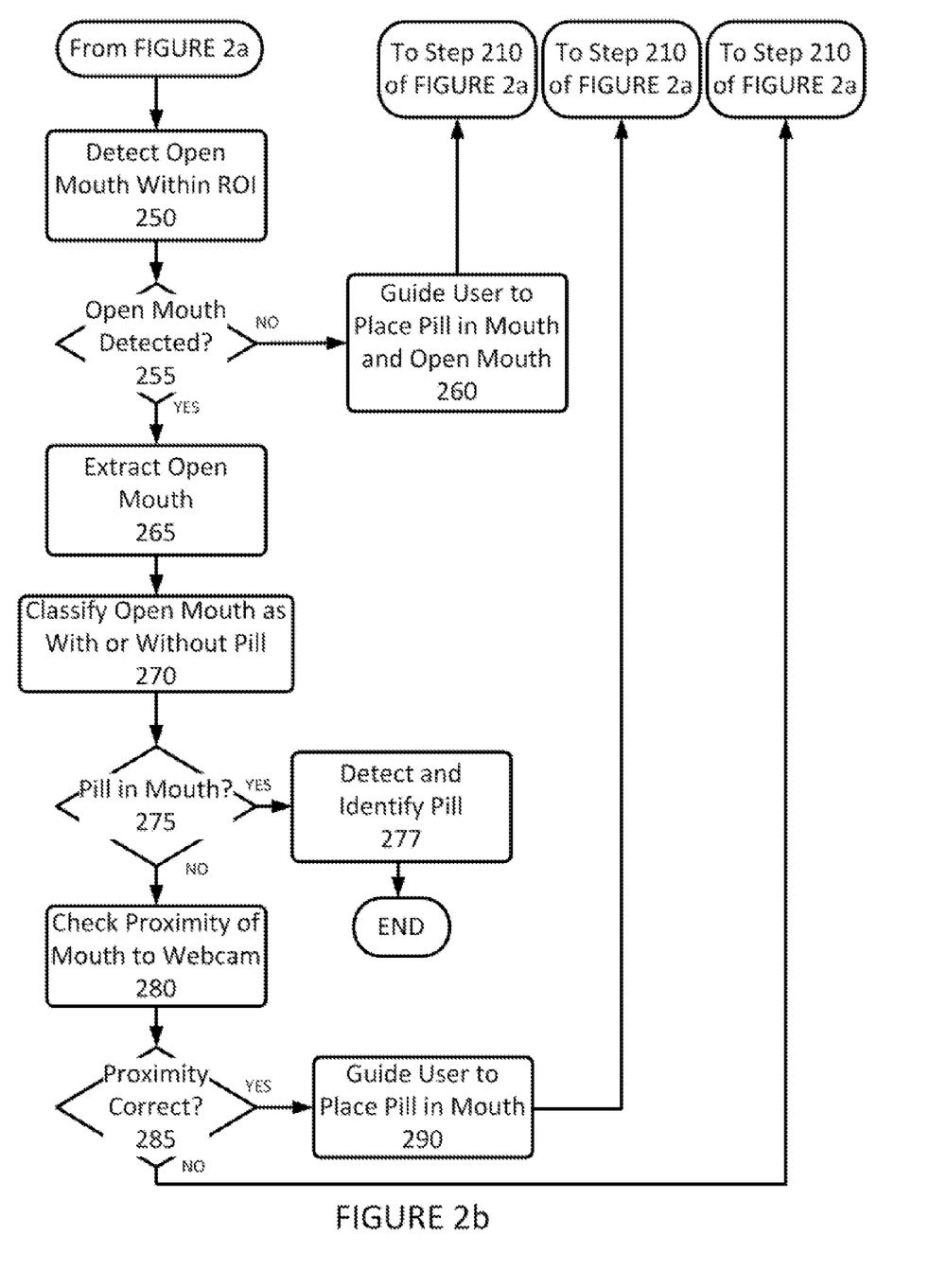

Of course, embodiments of the present invention may be employed when computing power is not a difficulty, as is set forth in FIGS. 2*a* and 2*b*, employing additional steps for actual pill tracking and identification. Referring to FIGS. 2*a* and 2*b*, a method for determining whether a user has placed a pill in their mouth for use in a more computationally sophisticated environment is presented. A user is prompted to place a medication pill in their mouth, and at step 210, a frame from a webcam is captured. While this particular embodiment of the invention notes that a single frame is captures, multiple frames may also be captured for use. Next, at step 220, face detection is performed to determine whether a face is present in the field of view. Such face detection is known to those of ordinary skill in the art. At step 225, an inquiry is made as to whether a face is in fact present in the field of view. If this inquiry is answered in the negative, and therefore it is determined that no face is present in the field of view, processing returns to step 210, and one or more additional webcam frames are captured.

If, on the other hand, the inquiry at step 225 is answered in the affirmative, and it is therefore determined that a face is present in the field of view, processing passes to step 230 where the proximity of the face to the webcam is determined by measuring a size of the face in the field of view. After measuring the size of the face, an inquiry is made at step 235 as to whether the face is within a range of correct distances from the webcam. If this inquiry is answered in the negative, and therefore it is determined that the face is not the correct distance from the webcam, processing moves to step 240 where the user is guided to reposition their face, and then processing returns to step 210, and one or more additional webcam frames are captured.

If, on the other hand, the inquiry at step 235 is answered in the positive, and it is therefore determined that the face is the correct distance from the webcam, processing passes to step 245 where the bottom half of the face is set as the Region of Interest (ROI). Processing then passes to step 247 where the position of a pill taken by the user (preferably placed in their mouth) is obtained from a pill tracking module. An inquiry is made at step 248 to determine whether such a pill is present within the ROI. If the inquiry at step 248 is answered in the negative, and it is therefore determined that a pill is not within the ROI, processing passes to step 249 where the user is guided to place the pill in their mouth (if not already there). Processing then returns to step 210.

If, however, the inquiry at step 248 is answered in the affirmative, and it is therefore determined that a pill is within the ROI, processing then passes to step 250, wherein the ROI is searched to determine whether the open mouth of the participant is present. At step 255 an inquiry is made to determine whether an open mouth of the participant has been detected. If this inquiry is answered in the negative, and therefore an open mouth of the participant has not been detected, processing passes to step 260 where the user is guided to place the pill in their mouth (if not already there) and open their mouth. Processing then returns to step 210.

If, on the other hand, the inquiry at step 255 is answered in the affirmative, and it is therefore determined that an open mouth of the user has been detected, processing passes to step 265 where the image of the open mouth of the user is extracted from the image. Once such extraction has taken place, processing passes to step 270 where the open mouth is classified as either an open mouth having a pill therein, or an open mouth not having a pill therein. At step 275 an inquiry is made to determine whether the pill is in the mouth of the user. If this inquiry is answered in the affirmative, and therefore the open mouth was classified at step 270 as an open mouth with a pill therein, processing passes to step 277 where the pill in the mouth of the user is individually detected, if possible. The pill may also be identified, if detected, employing a pill identification system, and may be based upon one or more of color, shape, texture, and the like. Once detected and identified then processing is complete, as it has been confirmed that a pill is in the mouth of the user.

One or more additional steps may be employed to further confirm ingestion of the pill by the user. Therefore, it may be confirmed whether the user drinks a glass of water, for example, and/or have the user open their mouth to determine that the pill is no longer in the user's mouth. Classification of the mouth of the user as a mouth without a pill in it may be employed similar to that in step 270 noted above. Once it is determined that the mouth is a mouth without a pill therein, processing can end. Further determinations may be made using audio and/or visual checking to determine whether a user has performed a swallowing action, employing classification similarly to that described with respect to the mouth.

If, on the other hand, the inquiry at step 275 is answered in the negative, and therefore the open mouth was classified in step 270 as an open mouth without a pill therein, processing passes to step 280 where proximity of the mouth of the user to the webcam is determined by measuring a size of the mouth. An inquiry is made at step 285 to determine whether the proximity of the mouth to the web cam is correct in accordance with the measurement of the mouth at step 280. If the inquiry at step 285 is answered in the affirmative, and it is therefore determined that the mouth of the user is a correct distance from the web cam, processing passes to step 290 where the user is guided to place the pill in their mouth (if not already there). Processing then returns to step 210.

If, on the other hand, the inquiry at step 285 is answered in the negative, and it is therefore determined that the mouth of the user is not a correct distance from the web cam, processing then returns to step 210.

Various guidance systems may be provided for positioning the user or pill, in accordance with one or more of the steps described above, as described in the above-mentioned U.S. patent application Ser. No. 12/815,037.

Figure 3:
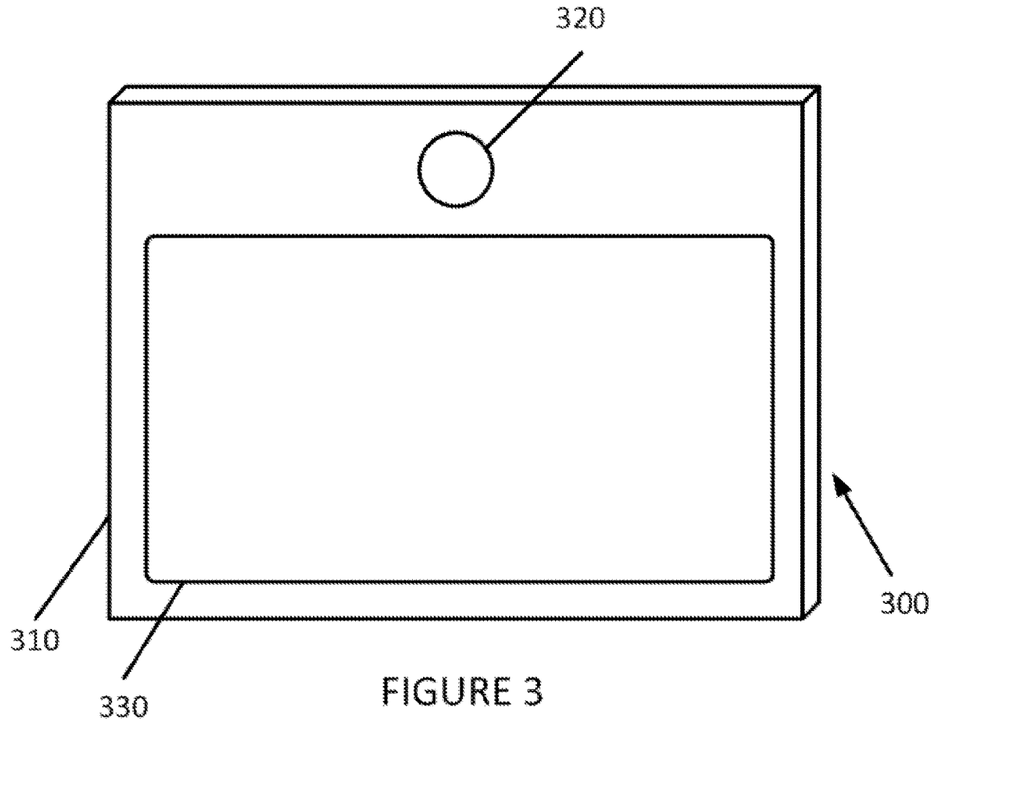
FIG. 3 depicts an exemplary hardware platform for implementation of the embodiments of the present invention.

Additionally, referring to FIG. 3, a display and image capture apparatus 300 that may be employed in accordance with one or more embodiments of the present invention for acquiring one or more images, and for displaying the one or more images and additional material, for performing processing in accordance with the various embodiments of the invention, and for storing computer program instructions, acquired data, and other information on a non-volatile computer readable storage medium is shown. Apparatus 300 preferably includes a housing 310, an image capture camera 320 and a display 330. Image capture camera 320 may comprise a single camera element, a stereo camera element or other appropriate image capture device. Other elements, as known to one of ordinary skill in the art, including ports, power attachments, processors for processing data, and the like may also be provided in accordance with apparatus 300. It is further contemplated in accordance with the various embodiments of the invention that apparatus may include one or more self-check mechanisms, including mechanisms for determining proper ambient light, direction and background of the camera and the background imaged by the camera, or other environmental issues that may be improved to further aid in the imaging of any images by apparatus 300. Additionally, if at any time it is determined that lighting conditions are too difficult for imaging apparatus 300, it may be possible to provide a light burst from a strobe or display to aid in illuminating the images to be captured. The above descriptions of the various embodiments of the invention will assume that such a display and image capture apparatus 300 may be employed. The invention, however, shall not be so limited and may be employed on any structure of image capture camera and display, whether contained in a single or multiple apparatuses, or any other appropriate system for capturing images and providing processing as described above. Furthermore, it is contemplated in accordance with the invention that image capture and processing may be implemented in a cloud computing environment, with an image capture device forwarding captured images to a remote location for storage and processing. Responses contemplated in accordance with the above description may be provided to the image capture device in manners known to those of ordinary skill in the art.

Therefore, in accordance with the invention, a method and apparatus are provided that allow for the automated confirmation of a user placing a pill in their mouth, for environments that have high or low computing power.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A method for confirming a pill in the mouth of a user, comprising:
    predefining one or more steps associated with confirming a pill in the mouth of a user, the one or more steps comprising at least proper identification of a medication pill, proper positioning of the face of the user, proper positioning of the open mouth of the user, and proper showing of whether there is a pill in the mouth of the user;
    displaying on a display one or more guidance instructions for properly positioning of a face of the user relative to the image capture camera;
    capturing a first set of one or more video frames by an image capture camera associated with the display;
    determining, by one or more processors in near real time from the first set of one or more video frames, that the user has properly positioned the face of the user in response to the one or more guidance instructions;
    confirming, by the one or more processors in near real time, that the face of the user is an expected face;
    in response to a confirmation that the face of the user is the expected face, displaying on the display one or more guidance instructions for positioning the medication pill relative to the image capture camera upon determination that the user has properly positioned the face of the user;
    capturing a second set of one or more video frames by the image capture device;
    determining, by the one or more processors in near real time, that the user has properly positioned the medication pill within the field of view in response to the one or more guidance instructions for positioning the medication pill, and that the medication pill is an expected medication pill from the second set of one or more video frames;
    setting a bottom portion of the face of the user as a region of interest, the region of interest including the mouth of the user, responsive to determining that the user has properly positioned their face in response to the one or more guidance instructions for positioning of the face of the user, that the user is the expected user, and that the medication pill is the expected medication pill;
    determining, by the one or more processors in near real time, that the mouth of the user in the region of interest is an open mouth from the second set of one or more video frames;
    subsequent to determining that the mouth of the user is the open mouth, extracting an image of the open mouth from the second set of one or more video frames, and classifying, by the one or more processors, the open mouth from the extracted image as a mouth without a pill therein;
    responsive to classifying the open mouth as the mouth without a pill therein, displaying on the display guidance for positioning the open mouth of the user relative to the image capture camera; and
    displaying on the display guidance to the user to place the medication pill in their mouth.

2. The method of claim 1, further comprising determining whether the user has performed a swallowing action.

3. The method of claim 1, further comprising determining the proximity of the mouth of the user to the image capture camera by measuring the size of the mouth of the user from the second set of one or more video frames.

4. The method of claim 1, further comprising the step of tracking the pill in the first and/or second set of one or more captured video frames.

5. The method of claim 4, further comprising guiding the user to position the pill, subsequent to determining that tracking of the pill cannot be confirmed.

6. A system for confirming a pill in the mouth of a user the system comprising:
    an image acquisition device operable to capture one or more video frames of a user;
    a display operable to display guidance for positioning of a face of the user relative to the image acquisition device in accordance with the captured one or more video frames, to display one or more guidance instructions for performing one or more steps associated with proper medication pill positioning; and
    a processor operable to:
    output, to the display, the one or more guidance instructions for positioning the face of the user relative to the image acquisition device in accordance with the captured one or more video frames, and guidance for positioning the open mouth of the user relative to the image acquisition device,
    receive, from the image acquisition device, a first one or more video frames of the user performing one or more steps associated with properly positioning the face of the user in response to the display on the display of the guidance instructions for positioning the face of the user and the open mouth of the user;
    determine in near real time whether the user has properly positioned their face within the field of view in response to the one or more guidance instructions for positioning the face of the user;
    receive, from the image acquisition device a second one or more video frames of the user;
    determine, in accordance with the second one or more video frames in near real time, whether the user has properly positioned the medication pill in response to the guidance instructions for performing one or more steps associated with proper medication pill positioning, thus allowing the processor to further confirm that the medication pill is an expected medication pill;

set a bottom portion of the face of the user as a region of interest, the region of interest including the mouth of the user, responsive to determining that the user has properly positioned their face in response to the one or more guidance instructions for positioning of the face of the user, classify in near real time, based on the second one or more video frames, the mouth of the user in the region of interest is an open mouth, subsequent to determining that the mouth of the user is the open mouth, extracting an image of the open mouth from the second one or more video frames, and classifying the open mouth from the extracted image as one of a mouth with a pill therein and a mouth without a pill therein, and output, to the display, guidance to the user to place a medication pill in their mouth when the open mouth of the user is classified as a mouth without a pill therein.

7. The system of claim 6, wherein the processor is further operable to confirm drinking a liquid by the user.

8. The system of claim 7, wherein the processor is further operable to confirm that the mouth of the user is empty after drinking the liquid.

9. The system of claim 6, wherein the processor is operable to confirm positioning of the mouth of the user relative to the displayed guidance in accordance with measuring the size of the mouth of the user from the one or more captured video frames.

10. The system of claim 6, wherein the processor is further operable to track the location of the medication pill through the one or more captured video frames.

11. The system of claim 10, wherein the processor is further operable to output to the display guidance to the user, wherein the guidance comprises instructions to position the medication pill when the processor is unable to track the medication pill through the one or more captured video frames.

12. The system of claim 6, wherein the processor is operable to confirm positioning of the face of the user relative to the displayed guidance in accordance with measuring the size of the face of the user from the one or more captured video frames.

13. A non-volatile computer readable storage medium having a computer program stored thereon, the computer program, when executed by a computer, causing the computer to perform the actions of:

predefining one or more steps associated with confirming a pill in the mouth of a user, the one or more steps comprising at least proper identification of a medication pill, proper positioning of the face of the user, proper positioning of the open mouth of the user, and proper showing of whether there is a pill in the mouth of the user;

displaying on a display one or more guidance instructions for properly positioning of a face of the user relative to the image capture camera;

capturing a first set of one or more video frames by an image capture camera associated with the display;

determining, in near real time from the first set of one or more video frames, whether the user has properly positioned the face of the user relative to the image capture camera in response to the one or more guidance instructions;

confirming, in near real time, that the face of the user is an expected face;

in response to a confirmation that the face of the user is the expected face, displaying on the display one or more guidance instructions for positioning of the medication pill relative to the image capture camera upon determination that the user has properly positioned the face of the user;

capturing a second set of one or more video frames of a user by an image capture device associated with the display;

determining, in near real time, whether the user has properly positioned the medication pill within the field of view in response to the one or more guidance instructions for positioning the medication, and that the medication pill is an expected medication pill from the second set of one or more video frames;

setting a bottom portion of the face of the user as a region of interest, the region of interest including the mouth of the user, responsive to determining that the user has properly positioned their face in response to the one or more guidance instructions for positioning of the face of the user, that the user is the expected user, and that the medication pill is the expected medication pill;

capturing a third set of one or more video frames by the image capture device;

confirming that the mouth of the user is an open mouth of the user within the region of interest from the third set of one or more video frames in near real time;

subsequent to determining that the mouth of the user is the open mouth, extracting an image of the open mouth from the third set of one or more video frames, and classifying the open mouth of the user as one of a mouth with a pill therein and a mouth without a pill therein in near real time; and responsive to classifying the open mouth of the user as the mouth without a pill therein, displaying on the display guidance for positioning the open mouth of the user relative to the image capture device and displaying on the display guidance to the user to place the medication pill in their mouth.

14. The non-volatile computer readable storage medium of claim 13, further comprising determining whether the user has performed a swallowing action.

15. The non-volatile computer readable storage medium of claim 13, further comprising determining the proximity of the mouth of the user to the image capture camera by measuring the size of the mouth of the user from the second set of one or more video frames.

16. The non-volatile computer readable storage medium of claim 13, further comprising tracking the pill in the first set of one or more captured video frames and the second set of one or more captured video frames.

17. The non-volatile computer readable storage medium of claim 13, further comprising tracking the pill in the mouth of the user.

18. The non-volatile computer readable storage medium of claim 17, further comprising identifying the tracked pill in the mouth of the user.

* * * * *